United States Patent [19]

Panek et al.

[11] 4,200,501

[45] Apr. 29, 1980

[54] SILICATE FOULING CONTROL DURING DIHYDRIC ALCOHOL DISTILLATION

[75] Inventors: Edward J. Panek, Trenton, Mich.; Werner O. Moll, Baton Rouge, La.; Lee H. Bergman, Grosse Ile; Siegfried P. Kersten, Trenton, both of Mich.

[73] Assignee: BASF Wyandotte Corporation, Wyandotte, Mich.

[21] Appl. No.: 889,778

[22] Filed: Mar. 24, 1978

[51] Int. Cl.$^2$ .................. B01D 3/34; C07C 29/26
[52] U.S. Cl. ........................... 203/7; 203/37; 568/868
[58] Field of Search ............ 203/7, 37, 36, 53, 18; 210/57; 568/868, 871, 861

[56] References Cited

U.S. PATENT DOCUMENTS

| | | | |
|---|---|---|---|
| 1,903,041 | 3/1933 | Hall et al. ........................... | 210/57 |
| 2,097,649 | 11/1937 | Solberg ................................ | 203/7 |
| 2,319,707 | 5/1943 | Reppe et al. ........................ | 568/861 |
| 2,629,686 | 2/1953 | Grosser ............................... | 568/868 |
| 2,768,214 | 10/1956 | McKinley et al. .................. | 568/868 |
| 2,788,373 | 4/1957 | Mills ................................... | 568/871 |
| 2,950,326 | 8/1960 | Hort .................................... | 568/861 |
| 3,412,160 | 11/1968 | Schierholt .......................... | 568/868 |
| 3,479,411 | 11/1969 | Adam et al. ........................ | 568/861 |
| 3,852,164 | 12/1974 | Chow et al. ........................ | 203/18 |
| 3,878,055 | 4/1975 | Cox et al. ........................... | 203/37 |

FOREIGN PATENT DOCUMENTS

45-10324  4/1970  Japan ......................... 203/37

Primary Examiner—Wilbur L. Bascomb, Jr.
Attorney, Agent, or Firm—Joseph D. Michaels; Arnold S. Weintraub

[57] ABSTRACT

Silicate fouling on the reboilers and trays and the distillation train used for the production of dihydric alcohols is arrested by the addition of caustic to the feed stream.

6 Claims, No Drawings

SILICATE FOULING CONTROL DURING DIHYDRIC ALCOHOL DISTILLATION

BACKGROUND OF THE INVENTION

I. Field of the Invention

The present invention pertains to processes for the manufacture of dihydric alcohols. More particularly, the present invention pertains to the production of butanediol. Even more particularly, the present invention pertains to a method for arresting silicate fouling during the production of butanediol.

II. Prior Art

Generally, the production of butanediol and similar dihydric alcohols contemplates the condensation reaction between an aldehyde or ketone with acetylene followed by the hydrogenation thereof, in the presence of a hydrogenation catalyst.

Typically, this catalytic reaction employs a catalyst which is supported on a silica base. Hence, the resulting aqueous solutions of crude butanediol contain some silicates which precipitate as the water is removed during the distillation process. The precipitation of the silicates occur, substantially, in the dewatering section of the distillation train or column. The silicates are deleterious in that they coat the reboiler tubes to such an extent that the heat transfer process is rendered impossible. The first distillation tower and its associated reboilers are those which are predominantly effected by the silicate precipitation.

The prior art has proposed some solutions to these problems. In steam generation plants silicate fouling is controlled by a lime/soda treatment and ion exchange resin treatment. Steam generation plants also employ phosphates to control silicate fouling. However, chemical plants have not adopted these known methods because of their cost, since uninterrupted service is not essential in chemical plants as it is in power plants. Thus, the chemical plants employ different methods. For example, silicates are cleaned out during shutdown periods, such as those forced by the silicate fouling itself and/or scheduled shutdowns. Other methods of overcoming fouling include the partial dismantling of the distillation train with the mechanical cleaning thereof or the utilization of a caustic boil out. The caustic boil out method typically uses a 5% to 10%, by weight, aqueous caustic medium with a minimum contact time of several hours at temperatures greater than 90° C. After the boil out is completed, the distillation towers and reboilers are rinsed to remove excess caustic. It is to be appreciated that this boil out method is not completely efficacious by virtue of the amount of aqueous caustic utilized; the contact times, as well as, the heat generation required for the temperatures. Thus, it is to be appreciated that a major advance in the art could be provided by a simplified method for reducing presilicate precipitation. It is to this end to which the present invention is directed.

SUMMARY OF THE INVENTION

In accordance with the present invention it has been found that silicate fouling in dihydric alcohol distillation trains can be minimized by the addition to the crude, aqueous dihydric alcohol solution of a minimal amount of caustic.

The caustic employed herein is an extremely dilute aqueous solution thereof containing, generally, from about 0.1 to $4 \times 10^{-5}$ weight percent of caustic. The control of the caustic addition is through regulation of the pH range. Preferably, the pH range is from 10.0 to about 12.8.

The amount of caustic to be added is governed by the tolerance in the distillation residue.

By the practice of the present invention, the distillation train is enabled to be run continuously; the volatile amines present in the crude butanediol solution or similar dihydric alcohol solution are more efficiently removed; the reboilers operate continuously at high efficiency; no crude product loss and the economic advantages over ion exchange resins.

For a more complete understanding of the present invention, reference is made to the following detailed description and accompanying examples.

DESCRIPTION OF THE PREFERRED EMBODIMENT

As heretofore noted, the present invention contemplates the addition of a minimal amount of caustic to a crude dihydric alcohol solution in a distillation train as a means for inhibiting silicate precipitation therewithin. More specifically, the present invention is particularly amenable to the inhibition and cessation of silicate fouling in a distillation train used for the preparation of butanediol.

The fundamental process to which the present invention is directed is that found in U.S. Pat. No. 2,319,707, the disclosure of which is hereby incorporated by reference.

As disclosed therewithin, aliphatic divalent alcohols are prepared by a method which contemplates the reaction between an aldehyde or ketone with acetylene, followed by the hydrogenation thereof in the presence of a hydrogenation catalyst. The disclosure therewithin is particularly directed to the process for the preparation of butanediol by the condensation reaction of formaldehyde, as an aqueous solution thereof, with acetylene followed by the hydrogenation thereof. Conventionally, two moles of formaldehyde are reacted with one mole of the acetylene.

The hydrogenation catalyst is deposited on a silica support.

The reaction is carried out in a distillation train which includes a tower as well as reboilers or a series thereof. Within the distillation train crude diol is obtained.

It should be noted that the present invention is particularly directed to the distillation trains used for the preparation of crude butanediol. However, it is to be understood that the present invention is efficacious in the preparation of aliphatic dihydric alcohols such as those described in the patent which employ hydrogenation catalysts deposited on a silica support.

In accordance with the present invention liquid caustic is directly fed into the crude dihydric alcohol solution contained in the distillation train to prevent the silicate fouling.

The caustic is employed as an aqueous solution thereof containing from about 0.1 percent, by weight, thereof to about $4.0 \times 10^{-5}$ weight percent thereof. Preferably, the aqueous solution of caustic contains at least about $4.0 \times 10^{-4}$ weight percent of caustic. The caustic solution can be added to the crude dihydric alcohol at any convenient point. Preferably, it is admixed with the crude dihydric alcohol feed at the inlet into the distillation train.

The amount of caustic solution to be added to the crude alcohol solution is a function of the pH of the alcohol solution to be maintained. Ordinarily, the process is carried out at a pH ranging from about 6 to 8. In practicing the present invention, the pH of the column is maintained at a pH ranging from about 9 to 14. Preferably, the pH is maintained at from about 10.0 to about 13. By regulating the pH, there is thereby provided control of the caustic addition.

In practicing the present invention, it has been observed that no caustic carry-over into the finished product occurs. Experimentation indicates that less than one-half part per million of sodium is present in the finished dihydric alcohol.

It is to be appreciated that by the addition of the caustic directly to the crude dihydric alcohol that silicate fouling is controlled in an effective and efficient manner. The present invention enables continuous running of the distillation train, thereby enabling total output to be increased. Furthermore, the amines present in the crude butanediol solution are efficiently removed. Furthermore, it has been found that the amine odor is negated and obviated. Also, because of the relatively inexpensive price of caustic versus ion exchange resins, the present method is extremely economical. Furthermore, there is no yield loss of the dihydric alcohol produced with the eventual result of the efficient operation and continuous operation of the reboiler without silicate fouling.

For a more complete understanding of the present invention, reference is made to the following examples thereof.

EXAMPLE I

For an approximate three-week period into a five column distillation train equipped with reboilers was fed crude aqueous butanediol. The pH of the crude feed to the column varied from 6.8 to 7.6, for about two weeks. Thereafter, the pH of the crude was elevated to range from 8.5 to 11.8 by the addition to the crude feed of a caustic solution containing about $4.0 \times 10^{-4}$ weight percent of caustic.

During this three-week period of the production of butanediol was in excess of 2,000,000 pounds.

Most important, however, after this duration of time the reboiler steam chest pressure had still not reached 250 pounds, this pressure at which reboiler clean out is necessary. Thus, the addition of the caustic solution to the crude feed inhibited silicate precipitation.

EXAMPLE II

For approximately a sixty-day period there was fed into a five column distillation train crude butanediol having a pH varying from 9.8 to 12.6. The pH of the crude feed was maintained by the addition to the feed of caustic solution containing about $4.0 \times 10^{-4}$ weight percent of caustic. During this sixty-day period the reboiler steam chest pressure only reached 160 pounds while production of butanediol was in excess of 4,000,000 pounds of butanediol. Thus, the efficacy of the present invention was further established.

Having, thus, described the invention, what is claimed is:

1. In a method for controlling silicate precipitation in a distillation process for the production of dihydric alcohols of the type wherein an aldehyde or ketone is reacted with acetylene followed by the hydrogenation thereof in the presence of a silica supported catalyst to provide a crude dihydric alcohol feed, the improvement comprising:
   distilling the crude dihydric alcohol feed in a distillation column,
   admixing with the crude dihydric alcohol feed an aqueous caustic solution, and
   recovering the dihydric alcohol.

2. The method of claim 1 wherein the caustic solution contains from about 0.1 to about $4.0 \times 10^{-5}$ weight percent of caustic.

3. The method of claim 2 wherein the caustic is present in a minimum amount of about $4.0 \times 10^{-4}$ percent, by weight, thereof.

4. The method of claim 1 wherein the dihydric alcohol is butanediol.

5. The method of claim 1 wherein the feed is introduced into the column at a pH ranging from about 10.0 to about 14.

6. The method of claim 5 wherein the pH of the feed ranges from about 10.0 to about 13.

* * * * *